United States Patent
Smith (10) Patent No.: US 9,138,542 B2
(45) Date of Patent: Sep. 22, 2015

(54) AUTOMATIC INJECTION DEVICE WITH TORSIONAL SPRING

(75) Inventor: Christopher James Smith, Cheshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 338 days.

(21) Appl. No.: 13/579,081

(22) PCT Filed: Feb. 15, 2011

(86) PCT No.: PCT/EP2011/052226
§ 371 (c)(1),
(2), (4) Date: Dec. 27, 2012

(87) PCT Pub. No.: WO2011/101349
PCT Pub. Date: Aug. 25, 2011

(65) Prior Publication Data
US 2013/0096513 A1  Apr. 18, 2013

Related U.S. Application Data

(60) Provisional application No. 61/305,436, filed on Feb. 17, 2010.

(30) Foreign Application Priority Data

Jul. 8, 2010  (EP) .................................... 10168927

(51) Int. Cl.
*A61M 5/315* (2006.01)
*A61M 5/20* (2006.01)

(52) U.S. Cl.
CPC ............... *A61M 5/3155* (2013.01); *A61M 5/20* (2013.01); *A61M 5/3156* (2013.01);

(Continued)

(58) Field of Classification Search
CPC ..... A61N 5/20; A61N 5/315; A61N 5/31553; A61N 5/31583; A61N 5/31593; A61N 5/3155; A61N 5/3156; A61N 5/31543; A61N 2005/202
USPC ................. 604/131, 134–135, 187, 207–208, 604/211–212, 214, 218, 232, 246
See application file for complete search history.

(56) References Cited

U.S. PATENT DOCUMENTS

2006/0276753 A1* 12/2006 Kronestedt et al. ........... 604/186
2007/0129687 A1*  6/2007 Marshall et al. .............. 604/207
(Continued)

FOREIGN PATENT DOCUMENTS

| WO | 02/053214 | 7/2002 |
| WO | 2006/045526 | 5/2006 |

(Continued)

OTHER PUBLICATIONS

International Search Report for Int. App. No. PCT/EP2011/052226, completed Jun. 9, 2011.

*Primary Examiner* — Kevin C Sirmons
*Assistant Examiner* — Amber Stiles
(74) *Attorney, Agent, or Firm* — McDonnell Boehnen Hulbert & Berghoff LLP (57) ABSTRACT

A semi-automatic "fixed" dose injection device is disclosed containing a reservoir of medicament, where a trigger controls the unwinding of a torsional spring to cause a predetermined injection of medicament from the reservoir through a disposable needle.

9 Claims, 3 Drawing Sheets (52) U.S. Cl.
CPC ...... *A61M 5/31553* (2013.01); *A61M 5/31583* (2013.01); *A61M 5/31593* (2013.01); *A61M 5/31543* (2013.01); *A61M 2005/202* (2013.01)

(56) References Cited

U.S. PATENT DOCUMENTS

2009/0227955 A1   9/2009   Hirschel et al.
2010/0298781 A1*  11/2010  Hogdahl et al. .............. 604/214
2011/0034878 A1*  2/2011   Radmer et al. ................ 604/192

FOREIGN PATENT DOCUMENTS

| WO | 2006/126902 | 11/2006 |
| WO | 2007/063342 | 6/2007 |
| WO | 2008/087071 | 7/2008 |

\* cited by examiner

AUTOMATIC INJECTION DEVICE WITH TORSIONAL SPRING

CROSS REFERENCE TO RELATED APPLICATIONS

The present application is a U.S. National Phase Application pursuant to 35 U.S.C. §371 of International Application No. PCT/EP2011/052226 filed Feb. 15, 2011, which claims priority to U.S. Provisional Patent Application No. 61/305,436 filed on Feb. 17, 2010 and European Patent Application No. 10168927.1 filed Jul. 8, 2010. The entire disclosure contents of these applications are herewith incorporated by reference into the present application.

FIELD OF INVENTION

This disclosure relates to a "fixed" dose injection device that may deliver a predetermined dose of medicament from a cartridge preferably through a single needle, particularly semi-automatically, when a user activates a trigger.

BACKGROUND

Multi-use and disposable injection devices are in common use for the delivery of injected medication. Such devices are needed so that a user may take repeated doses of a medication at specific time intervals, for example rapid acting or basal insulins, GLP-1, heparin, etc. Conducting repeated injections is both inconvenient and confusing to some users, especially those users with visual imparity or cognitive deficiencies.

Accordingly, them is a strong need to provide injection devices that are easy to use and that allow a user to set a predetermined "fixed" dose of a medicament.

It is an object of this disclosure to provide a novel injection device, preferably an improved injection device.

This object may be achieved by the subject matter of the independent claims. Advantageous embodiments and refinements are the subject matter of the dependent claims.

This disclosure facilitates solving the above-described problems, for example, by providing a, preferably semi-automatic, injection device were the user can only dial predetermined doses of medicament. These and other advantages will become evident from the following more detailed description of the invention.

The claimed subject matter does have various advantages which, inter alia, will become apparent from the description below.

SUMMARY

According to an exemplary arrangement the injection device of this disclosure, for example a fixed dose injection device, is a multiple use device, meaning that a number of injections can be administered from the same medicament container or cartridge until that container is empty. The device may be made as a disposable variant Where the entire device is discarded once the medicament container is empty, or as a reusable variant, where the user can discard and replace the empty medicament container and reuse the device mechanism. For each separate injection the user may manually attach a new sterile needle. After the injection this needle may be manually removed and discarded.

The injection device of this disclosure may be a "semi-automatic" injection device. This means that the liquid medication will be delivered automatically through the needle by the action of stored energy, preferably from a, e.g. wound, dose spring, within the device. The user, however, may have to manually insert the needle before the injection, remove the needle after the injection, and/or activate the trigger in order to complete the injection. The user may also have to "recharge" the dose spring between doses. This may be accomplished as part of the dose setting procedure. Energy may be stored in the dose spring during dose setting, which energy may be released for injecting the dose.

Using the "fixed" dose mechanism of this disclosure it is possible to configure the mechanism where the fixed dose is anywhere between 0.01 ml to approximately 0.30 ml (1 insulin unit to about 30 insulin units). Because the disclosed device delivers only a predetermined fixed dose, the dose dial may have only markings for the single predetermined fixed dose. No other dose markings are needed. The user may rotate the dose dial to the marking for the fixed dose whereupon the dose dial clicks as a ratchet on the drive shaft engages a gear tooth on the gear. At this point the dose dial expediently remains in the "set" position. The user may be prevented from dialing doses smaller than the fixed dose by the action of the dose spring, e.g. a torsion action. If the user does not rotate the dose dial sufficiently to engage the dose dial ratchet, then as soon as the user releases the dose dial the dose spring will rotate the dose dial back to the zero unit position. The user may be prevented from dialing larger doses by one or more mechanical stops limiting the travel of the dose dial.

The setting of the fixed predetermined dose may be controlled by the interaction of the gear, the trigger, and the drive shaft, which may be, preferably permanently, connected to the dose dial. During dose setting the gear may be prevented from rotation by the trigger. The trigger may have a set of teeth on an inner surface that engages complementary teeth on the outer side of the gear. The drive shaft preferably has a ratchet arm that engages one or more limited number of teeth, which are preferably equally spaced an angle $\alpha$ from each other. The teeth may be provided on the proximal side and/or on an inner surface of the gear. Preferably, this angle $\alpha$ is at least about 20 degrees, most preferably in the range of about 30 degrees to about 180 degrees. The minimum end of the preferable range may be determined by the smallest rotation that can be easily distinguished by the user so it is clear whether or not a dose has been set. The maximum end of the preferable range may be determined by the greatest rotation that a user can comfortably achieve in one single movement without significantly altering their grip during dose setting. For example, a 120 degrees rotation may be more comfortable for a user, but 180 degrees is also possible. Furthermore, the angle $\alpha$ is preferably a divisor of 360 degrees so that the teeth may be evenly spaced around the inner side of the gear. In variable dose injectors, each tooth on the inner side of a gear usually corresponds to one index of the dose dial, for example, 0.01 ml (1 insulin unit) for a 21 unit configuration or 0.02 ml (2 insulin units) for a 42 unit version. In these non-fixed dose devices, the angle between the teeth is always less than 16 degrees. This is in contrast to this disclosure where the angle $\alpha$ is preferably always greater than about 20 degrees. When dialing a dose in these prior art devices the user rotates the dose dial and the drive shaft ratchet clicks over the desired number of teeth. In this manner a number of different doses could be set each time the device is used. This is preferably not possible in the fixed dose device of this disclosure, which requires rotation to overcome only a single tooth to set the same "fixed" predetermined dose each time the device is used. Preferably, a rotation which may overcome more than one tooth is prevented.

Rotating the dose dial may also store energy, e.g. torsional energy, within the dose spring. When the trigger is activated, e.g. pressed, the trigger and the gear may disengage. Particularly, the teeth on the gear, preferably outer teeth on the gear, may disengage from the corresponding teeth on the trigger and the gear becomes free to rotate. The dose spring may drive the drive shaft in rotation, which in turn preferably rotates the gear, particularly, because the ratchet arm is engaged with teeth of the gear, preferably inner teeth of the gear. The gear may have one or more internal threads that are engaged with one or more external threads of the plunger. The pitch β of the respective thread, preferably of the threads of the plunger and/or of the gear, may be selected and matched so that rotation of the gear, which is expediently constrained in the axial direction, will cause the non-rotating plunger to move axially. Preferably, the angle α and the pitch β are selected so that the axial advance of the plunger is set to a particular value corresponding to the desired fixed dose. The axial advance of the plunger may be determined by the calculation:

$$\text{Advance} = (\alpha/360) \times \beta$$

More specifically, angle α is preferably in the range from about 30 degrees to about 180 degrees. The pitch β of a thread on plunger and/or gear is preferably from about 1.5 mm to about 12 mm. Expressed differently, it is preferred that the ratio of α/β is in the range from about 10 to about 20 degrees/mm.

Preferably the limited number of teeth on the gear that dictate or contribute to the "fixed" predetermined dose are evenly spaced around the circumference of the gear. The angle α between these teeth preferably corresponds to the angle that the drive shaft will be rotated when the fixed dose is delivered. For example, if the gear contains four teeth then the angle α between them will be 90°. If the drive plunger thread pitch β is 6 mm then a 90° rotation will cause the plunger to advance by a "fixed" increment of 1.5 mm. By appropriate design of the number of gear teeth, and the thread pitch β between the gear and the plunger, the nominal volume of the fixed dose can be altered. A particular advantage of devices disclosed herein over prior art devices is that small doses (for example doses<0.05 ml or 5 insulin units) can be delivered with improved dose accuracy. This may be achieved by the combination of large angles α and small thread pitch β. Large angles of α mean that any angular error (fix example variability due to the manufacturing tolerances, e.g. of either gear or ratchet arm) represents only a small percentage of the angle α. Combining this with small values of thread pitch β will produce the small advance of plunger necessary for delivering small doses. A further advantage of the larger angle of α is that the, preferably torsional, spring, which will provide the energy required for automatic dose delivery, is loaded over a longer movement. This means that the dialing torque that the user must apply to charge the spring with a given amount of energy is reduced compared to a device with a smaller value of α.

As mentioned, if the user fails to rotate the dose dial by an angle sufficient to engage the ratchet arm of the drive shaft, then the dose will not be set. The dose spring will rotate the dose dial and drive shaft back to the zero unit position of the dose dial. Therefore, it will be impossible for the user to set any dose below the "fixed dose" determined by the spacing of the gear teeth. The fact that the dose dial immediately rotates back to zero units, rather than remaining at the marker for the fixed dose, will alert the user to the fact that the dose was not properly set. This should prevent the user from attempting to deliver a zero dose. This places an ergonomic limit on how far the user can be expected to rotate the dose dial in one movement. It is therefore preferred that there should be a minimum of two gear teeth. This would mean that the maximum rotation the user would have to apply would be 180°.

The maximum dose of the device may be limited by adding features that will limit the rotation of the dose dial (and hence drive shaft). This rotation limit, will be designed to ensure that the user will always be able to dial the ratchet arm beyond one gear tooth (irrespective of any manufacturing tolerances) and not beyond a second tooth. In practice this means that the rotation stop may be set in the region α to 2α and with sufficient clearance to ensure that the effect of manufacturing variability does not take the rotation stop outside of this range. Preferably the rotation stop will be set towards the lower end of the range so that the user does not dial significantly beyond the first gear tooth. A small amount of over rotation is required in order to guarantee that the ratchet arm will engage. Therefore, the rotational limit of the dose dial would be set to an angle slightly greater than the angle α between the gear teeth. However, this over travel does not contribute to any dose accuracy error of the pen because when the user releases the dose dial the dose spring will immediately rotate the dose dial and drive shaft back until the ratchet arm contacts the gear tooth. Given that the trigger is not pressed at this point then the rotation of the drive shaft does not rotate the gear and hence no medicament is dispensed. A number of options exist for adding rotation restricting features, for example features could be added to the dose dial and the body, or to the drive shaft and the body.

The plunger may be prevented from rotation by features in a reset dial, preferably fingers that engage flats along the axis of the plunger. Therefore, rotation of the gear may cause the plunger to advance along its threaded connection to the gear and this dispenses liquid from the medicament container as it moves a piston or bung in the distal direction. If the trigger is released at any point during the delivery of the dose a trigger spring may force the teeth on the trigger to reengage the gear, preferably to reengage outer teeth on the gear, and cause delivery to stop. Pressing the trigger again will continue the delivery, until the dose has been delivered.

A further advantage of devices disclosed herein over the prior art is that the trigger and gear may be configured so that the trigger only needs a single activation to delivery the full "fixed" dose, without requiring the user to hold the trigger in the active position. Variable dose devices usually have a trigger that can re-engage with the gear at any point that corresponds to a multiple of the smallest dose that the user can dial and deliver, i.e. if the inner surface of the gear (which engages the ratchet arm) has 24 gear teeth then the outer surface of the gear (which engages the trigger) must also have 24 gear teeth. Therefore, once the dose delivery has been initiated the user may release the trigger button at any time during dose delivery and the delivery will stop. The possibility of stopping the dose delivery may lead to dose errors where the user mistakenly or deliberately delivers an incomplete dose.

A further embodiment of the proposed fixed dose device seeks to improve the usability of the device so that the entire dose is delivered with one push of the trigger, e.g. a trigger button, irrespective of whether the trigger is held. This is accomplished by modifying the trigger mechanism. The teeth of the gear and the trigger may be replaced by a set of male & female features, e.g. teeth and grooves, on the gear & trigger. The features would be equally spaced around the circumference of the gear and the number of features would match the number of dose setting teeth of the gear/drive shaft interface. The proposed features would make it impossible for the trigger to re-engage the gear until the gear has completed its fixed rotation. Therefore, the user would press the trigger once to start the delivery, and then the complete dose would deliver automatically, irrespective of whether the user holds the trigger or not. Because the trigger may automatically slide back into place at the end of the dose, e.g. driven by the trigger spring, the user will receive visual confirmation that the dose has been fully delivered. In addition the trigger could be designed to click when it re-engages the gear, providing audible confirmation as well.

After the medicament container has been emptied the user will be able to reset the plunger to its initial position and a new medicament container can then be loaded into the device and the device can be reused.

A titration pen variant of the fixed dose device of this disclosure is also possible. In this variant the maximum rotation of the dose is not limited to allowing the ratchet arm to rotate beyond only one gear tooth. Instead the maximum rotation is designed to allow the ratchet arm to rotate beyond multiple gear teeth. This number of teeth that the ratchet arm may rotate past would correspond to the number of "titration" doses that the user desired to set. The titration device may be configured to allow 5 or less, e.g. 3 or less, titration doses to be set by a user. For example, if the device were designed such that a 90° rotation of the plunger delivers a dose of 5 units and the gear was designed with 4 gear teeth then the ratchet arm would engage a gear tooth every 90°. Setting the maximum rotation of the dose dial to 270° would enable three different doses to be set by the user: 5 units, 10 units or 15 units. To reach the 15 unit dose the user would turn the dose dial through 3 clicks of the drive shaft ratchet, corresponding to 270°. However, unlike the single fixed dose device this could be achieved by the user in a number of steps. It is therefore not necessary to limit total rotation to 180° (although each sub dose dialed should be less than 180°). In the titration embodiment delivery of doses in between the fixed titration doses is prevented in a similar manner as preventing under doses for the fixed dose device. If the user dials a dose in between the fixed titration doses the dose spring will rotate the dose dial and the drive shaft back until the ratchet arm engages at the next gear tooth, corresponding to the next lowest titration dose. The set dose would be clearly displayed to the user by the dose dial, so it would be clear that the higher dose had not been set.

A semi-automatic feature of devices disclosed herein has certain advantages over known delivery devices that rely on a user's manual pressing of an injection button. This creates difficulty or even pain for elderly use or those with reduced manual dexterity. Also, any shaking of the hand while pressing the dose button will cause movement of the device and needle, making the injection more painful. A semi-automatic device removes this problem. The user supplies the energy to provide the injection during the dose setting stage. This may use larger sets of muscles, arms and wrists rather than finger or thumb power, and should therefore be easier for patients. Also, the energy is applied before the needle is injected into the body. Therefore, it does not matter if there is some movement or shaking of the device.

In prior known manually driven devices it is possible that the user does not press the dose dial fully inwards and therefore may deliver an under dose. With a semi-automatic device of this disclosure the full dose is achieved more consistently. Likewise, dose accuracy in prior devices that require pressing a manual dose button can cause the user to not behave consistently where they will press and hold the button for varying times. Different button hold times allow different expansion of the bung or piston, e.g. a rubber bung or a rubber piston, within the medicament container or cartridge and this has the potential to create variability between doses. The semi-automatic feature of devices disclosed herein eliminates this variable because the dose spring will work independently of the user, particularly during the injection. Therefore, the forces applied to the bung or piston of the medicament container during dose delivery may be determined by the design of the device, irrespective of forces applied to the trigger button.

In the following text, a set of particularly advantageous aspects of the injection device is provided by making use of numbers to facilitate making references to the respective aspects.

1. A fixed dose injection device comprising the following in combination,
   a. a housing; and
   b. a dose setting/injecting assembly comprising,
      i. a rotatable gear having at least two teeth offset from an each other at an angle $\alpha$ that corresponds to a predetermined fixed dose of medicament, where the gear wheel is fixed axially in the housing;
      a plunger threadedly engaged with the rotatable gear having a pitch $\beta$ that is matched with angle $\alpha$ so that the plunger moves distally during dose delivery a distance equal to the predetermined dose;
      iii. a torsional spring, and a drive shaft; and
      iv. a trigger connected to the rotatable gear such that when the trigger is activated the torsional spring unwinds and causes the gear wheel to rotate through angle $\alpha$ and to move the plunger distally to deliver the predetermined fixed dose.

2. The injection device of aspect 1 wherein a medicament housing is connected to the housing and holds a cartridge of medicament.

3. The injection device of aspect 1 wherein the angle $\alpha$ is from about 20 degrees to about 180 degrees.

4. The injection device of aspect 1 wherein the ratio of $\alpha/\beta$ is in the range from about 10 to about 20 degrees/mm.

5. An fixed dose titration infection device comprising the following in combination,
   a. a housing; and
   b. a dose setting/injecting assembly comprising,
      i. a rotatable gear having at least a first, a second, and a third tooth offset from an each other at an angle $\alpha$ that corresponds to a predetermined fixed dose of medicament, where the gear wheel is fixed axially in the housing;
      ii. a drive shaft having a ratchet arm that is configured engage either the first, the second or the third tooth during dose setting;
      iii. a plunger threadedly engaged with the rotatable gear having a of pitch $\beta$ that is matched with angle $\alpha$ so that the plunger moves distally during dose delivery a distance equal to one or more multiples of the predetermined dose;
      iv. a torsional spring; and
      v. a trigger connected to the rotatable gear such that when the trigger is activated the torsional spring unwinds and causes the gear wheel to rotate through angle $\alpha$ and to move the plunger distally to deliver the predetermined fixed dose;

Features describe above or below in connection with different aspects, embodiments etc. may, of course, be combined with features described in connection with other aspects, embodiments etc. or with a combination of such features even if such a combination is not explicitly described herein.

The advantages mentioned above as well as other advantages of various aspects of the present disclosure will become apparent to those of ordinary skill in the art by reading the following detailed description, with appropriate reference to the accompanying drawings.

BRIEF DESCRIPTION OF THE FIGURES

Exemplary embodiments are described herein with reference to the drawings, in which.

DETAILED DESCRIPTION

Figure 1:
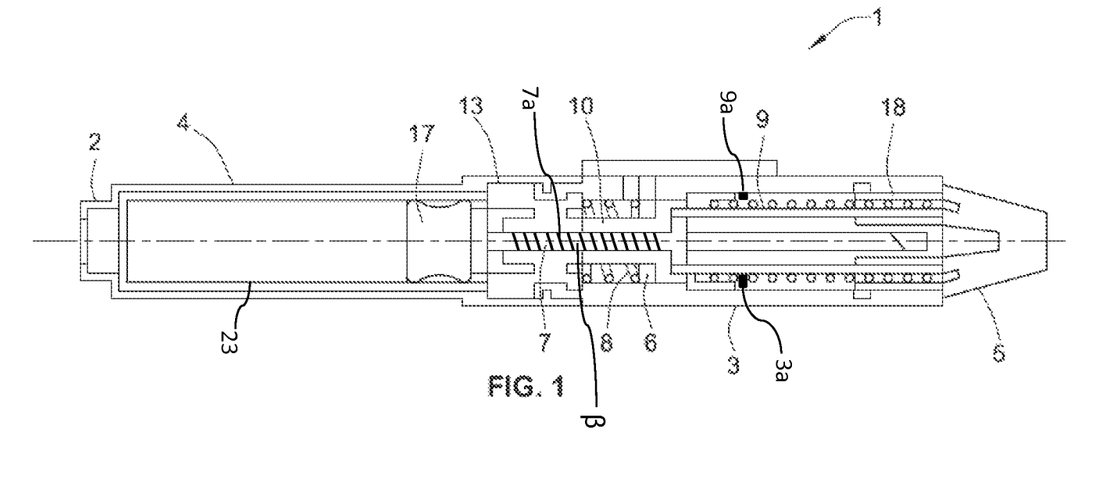
FIG. 1 illustrates one possible embodiment of the "fixed" dose injection device of this disclosure.

A schematic cross section of one embodiment of the "fixed" dose injection device 1 of this disclosure is illustrated in FIG. 1. The device comprises two main assemblies; a dose setting/injecting assembly; and a cartridge holder 4. The device comprises a body 3. The dose setting/injecting assembly may be at least partly retained or housed in body 3. The dose setting and cartridge holder assemblies are similar in design and operation to that described in U.S. Pat. No. 5,104,380 with significant differences. One significant difference is that the disclosed device is configured to allow the user to set only a fixed, predetermined dose, as opposed to a large number of different doses. This difference in operation may result from a novel design of gear 10. This novel design of the gear is best viewed in FIG. 2.

A cartridge 23 is retained in the cartridge holder. A piston 17 may be arranged and movably retained in the cartridge 23. The cartridge 23 expediently holds a medicament which is to be dispensed from the device 1. The piston 17 may seal the medicament within the cartridge 23.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy.

wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3) Glu(B29) human insulin; Lys(B28), Pro(B29) human insulin; Asp(B28) human insulin; human insulin, wherein praline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A disposable injection needle assembly (not shown) is attached to hub 2, which preferably has external threads that engage similar pitch threads inside a female hub on the disposable needle assembly. The setting of the fixed dose within injection device 1 is controlled by the interaction of the drive shaft 9, which is preferably permanently connected to dose dial 5, and gear 10, which is expediently slidably engaged with trigger 6. During dose setting, gear 10 is prevented from rotation by the interaction of components on the gear and trigger. Drive shaft 9 features a ratchet arm 12 (see FIG. 2) that engages teeth 11 on an inner surface 14 of gear 10. Each tooth 11 is separate by an angle α from the next tooth, shown in FIG. 2 as 90°. Each tooth of the gear corresponds to one predetermined fixed dose. By appropriate design of the number of gear teeth, as described above, and the thread pitch between the gear and the plunger, the nominal volume of the fixed dose can be altered.

Movement of the plunger 7 is achieved by energy stored in a helical torsional spring 18, which is twisted as the dose of medicament to be injected from the cartridge 23 is set by rotation of dose dial 5. The dose dial can turn about a graduated sleeve or the drive shaft and may contain printed graduations that correspond to the fixed dose. Body 3 can have a lens or one or more windows (not explicitly shown) through which graduations on the sleeve or shaft can be read to show that the fixed dose has been set.

Figure 2:
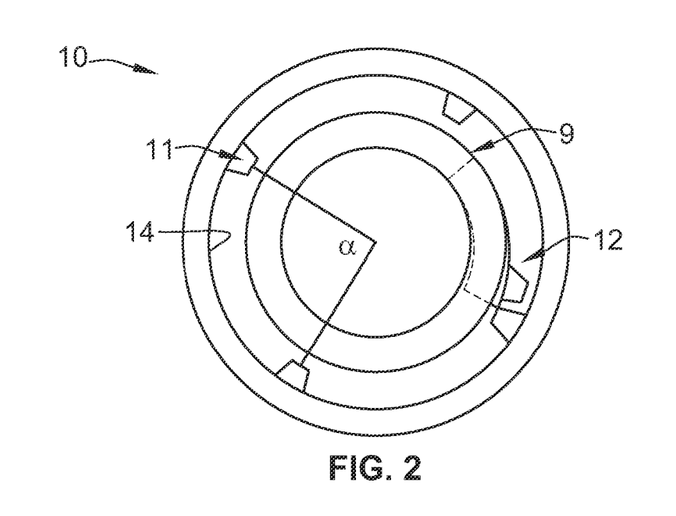
FIG. 2 illustrates a cross sectional view through the "fixed" dose injection device of this disclosure showing a fixed dose stationary gear, the drive shaft, and ratchet arm engaging one of the four teeth on the inner surface of the gear.
Figure 3:
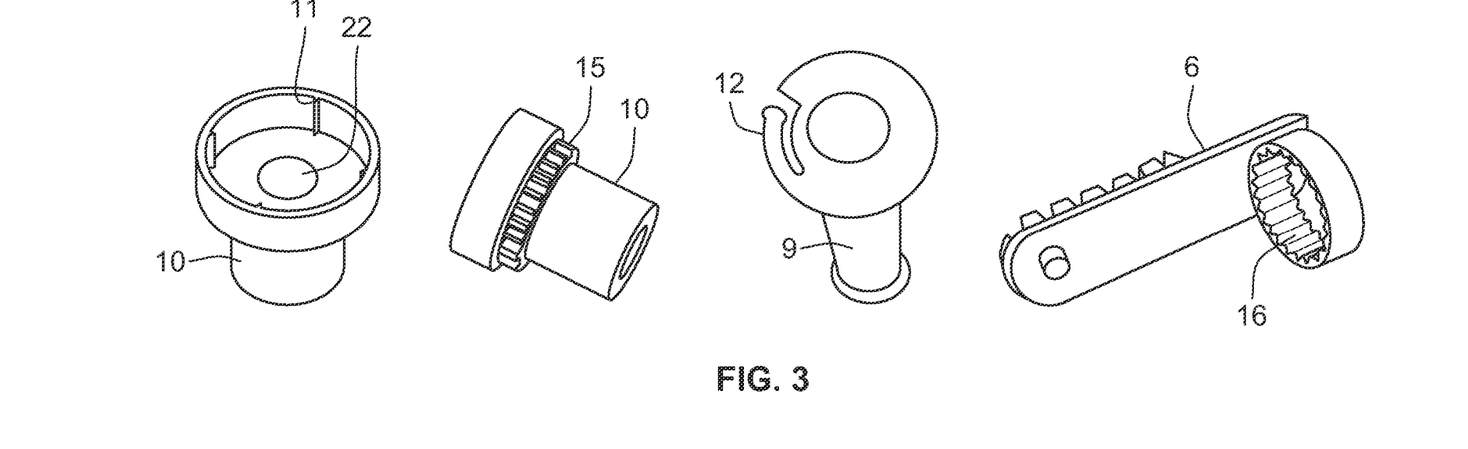
FIG. 3 illustrates possible embodiments of the drive shaft, gear and trigger of the dose setting assembly of this disclosure.
Figure 4:
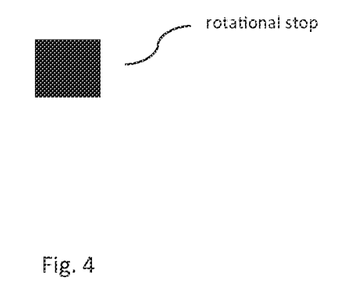
FIG. 4 illustrates a rotational stop of this disclosure.

When dialing a dose the user rotates dose dial 5, which causes the connected drive shaft 9 and ratchet arm 12 to rotate and click over one of the teeth 11 in gear 10. The user may rotate the dose dial by the angle α or an angle which is slightly greater than α. The user may be prevented from rotating the dose dial 5 by 2α by a rotational stop as illustrated in FIG. 4, which may be provided in the body, for example. Thus, setting of a dose exceeding the fixed dose may be prevented. Alternatively, instead of providing a fixed dose device where only one dose may be dialed, a titration device may be provided as described further above, which is designed such that a limited number, e.g. 5 or less, preferably 3 or less, titration doses may be dialed by the user. Rotating the dose dial also stores torsional energy within the corresponding dose spring 18 that is fastened to the dose dial. This stored torsional energy is used to automatically deliver the medicament dose when trigger 6 is pressed or otherwise activated causing the spring 18 to unwind and returning the dose dial 5 and the drive shaft 9 to the initial zero position. When the trigger 6 is activated, teeth 16 disengage from teeth 15 on gear 10 and the gear becomes free to rotate with drive shaft 9 (see FIG. 3).

The stored energy of the dose spring 18 drives the drive shaft 9 in rotation, which in turn rotates the gear 10. The gear 10 has a central threaded opening 22 that is in threaded engagement with plunger 7. The plunger is prevented from rotation by features in reset dial 13. Preferably, the reset dial 13 contains two protrusions (not shown) that consist of opposed flats that engage two longitudinal grooves on opposed sides along the length of the drive plunger 7. When the corresponding cartridge holder 4 is attached to the body 3, the reset dial 13 is prevented from rotation relative to the body 3. Thus, when the cartridge holder 4 is connected to the body 3, rotation of the drive plunger 7 is prevented. Because the drive plunger 7 cannot rotate and the gear 10 cannot move axially, the rotation of the gear 10 causes the drive plunger 7 to advance along its thread 7a having pitch β that is engaged with the thread in gear 10 in an axial distal direction exerting force on piston 17 inside cartridge 23. This causes the pressure in the cartridge to increase and liquid medicament is dispensed from the distal end of the cartridge into an attached needle. The pitch β may be 6 mm, for example, resulting in an axial displacement of the plunger by 1.5 mm when the gear is rotated by the angle α of 90°. If the trigger 6 is released at any point during the delivery of the set dose, teeth 15 and 16 will re-engage stopping the rotation of gear 10 and thus stopping the delivery of medicament. When the trigger 6 is being held by the user in the activated position a trigger spring 8 may tend to push the trigger 6 into re-engagement with gear teeth 15 on the outside of the gear 10. When the trigger 6 is released by the user, the trigger spring 8 will re-engage trigger and gear. Pressing the trigger again will continue the delivery until all of the dialed units have been delivered. The injection of medicament is complete when the dose dial 5 reaches a rotational stop (not explicitly shown) with respect to the body 3. This stop position corresponds to the "zero dose selected" position of the dose dial 5.

If the user fails to rotate the dose dial by an angle sufficient to engage the ratchet arm 12 of the drive shaft 9, then the dose will not be set. The dose spring will rotate the dose dial and drive shaft back to the zero unit position of the dose dial. Therefore, it will be impossible for the user to set any dose below the "fixed dose" determined by the spacing of the gear teeth Upon injection, axial movement of the plunger 7 along the quick pitch thread, which may be provided in opening 22, accompanies rotation of gear 10 and drive shaft 9 since the plunger 7 cannot rotate in the reset dial 13. Thus, the plunger is driven into the cartridge. expelling the fixed dose of medicament from the cartlidge. The injection of medicament is complete when dose dial 5 reaches a rotational stop (not explicitly shown) with respect to the body 3. The stop position corresponds to the "zero dose selected" position of dose dial 5. When the dose dial 5 reaches its rotational stop on the pen body, the plunger remains part-way along the inside of the cartridge. The procedure can be repeated until the cartridge is exhausted, after which the cartridge can be replaced by removing the cartridge holder from the dose dialing assembly.

In some cases, the requirement to hold down the trigger until the injection is complete may be considered undesirable and therefore an alternate embodiment would include a configuration that prevents the trigger from reengaging with the gears even though the user releases the trigger. This may, for example, be accomplished by including a detent mechanism whereby pressing the trigger causes it to bump-over a detent so that it will remain in the forwards position even if the user releases the trigger, e.g. a trigger button. The detent could be designed to disengage only when the drive shall or dose dial have returned to their initial, zero, positions. This would enable the complete injection to be delivered with only a single press of the trigger (without the need to hold the trigger forwards). A further advantage would be that the return of the trigger to its initial position would give the user additional visual and audible feedback to indicate that the dose is complete.

Alternatively or additionally, the fixed dose device may be configured so that the entire dose is delivered with one push of the trigger 6, e.g. a trigger button, irrespective of whether the trigger is held or detented as described above. This may be accomplished by modifying the trigger mechanism. The teeth 15 of the gear 10 and the teeth 16 of the trigger 6 may be replaced by a set of male and female features (not explicitly shown), e.g. teeth and grooves, on the gear 10 and on the trigger 6. The features may be equally spaced around the circumference of the gear 10. The number of features preferably matches the number of gear teeth 11. These features are preferably designed such that it is impossible for the trigger 6 to re-engage the gear 10 until the gear has completed its fixed rotation for delivering the fixed dose. Therefore, the user would press the trigger 6 once to start the delivery, and then the complete dose may be delivered automatically, irrespective of whether the user holds the trigger 6 or not. Because the trigger 6 may automatically slide back into place at the end of the dose, e.g. driven by the trigger spring 8, the user will receive visual confirmation that the dose has been fully delivered.

The reset dial 13 not only prevents the plunger from rotation during that movement, but it also acts as a means fix retracting the drive plunger 7 back into the body 3 thus resetting the device. When the cartridge holder 4 is attached to the body 3 the reset dial 13 is restrained against rotation in the body 3 by a locking member (not explicitly shown) fitted into the reset dial 13. When the cartridge holder 4 is removed the locking member is unrestrained and allows rotation of the reset dial 13. The drive plunger 7 may be prevented from rotation relative to the reset dial 13 by the engagement of reset dial protrusions and drive plunger longitudinal moves (not explicitly shown). The drive plunger 7 is threadedly engaged to the gear 10, which is fixed in rotation relative to the body 3 by the engagement of gear teeth 15 and trigger teeth 16. Rotation of the reset dial 13 causes the drive plunger 7 to rotate which causes it to wind up the thread in the gear 10, thus retracting the drive plunger 7 back into the body 3.

Exemplary embodiments of the present disclosure have been described. Those skilled in the art will understand, however, that changes and modifications may be made to these embodiments without departing from the true scope and spirit of the subject matter, which is defined by the claims.

The invention claimed is:

1. A fixed dose injection device comprising the following in combination,
   a. a housing; and
   b. a dose setting and injecting assembly comprising,
      i. a rotatable gear having only at least two teeth offset from each other at an angle α that corresponds to only one predetermined fixed dose of medicament, where the rotatable gear is fixed axially in the housing;
      ii. a plunger threadedly engaged with the rotatable gear having a pitch β that is matched with angle α so that the plunger moves distally during dose delivery a distance corresponding to the only one predetermined fixed dose;
      iii. a torsional spring, and a drive shaft wherein the torsional spring rotates the drive shaft back to a zero position if the drive shaft is rotated by an angle smaller than α during dose dialing such that dialing doses smaller than the only one predetermined fixed dose is prevented;
      iv. a trigger connected to the rotatable gear such that when the trigger is activated the torsional spring unwinds and causes the rotatable gear to rotate through angle α and to move the plunger distally to deliver the only one predetermined fixed dose; and
      v. a rotation stop that limits the rotation of the drive shaft, allowing a rotation beyond one tooth and preventing a rotation beyond more than one tooth of the rotatable gear such that setting a dose exceeding the only one predetermined fixed dose is prevented.

2. The injection device of claim 1 wherein a medicament housing is connected to the housing and holds a cartridge of medicament.

3. The injection device of claim 1 wherein the angle α is from 20 degrees to 180 degrees.

4. The injection device of claim 1 wherein a ratio of α/β is in the range from 10 to 20 degrees/mm.

5. The injection device of claim 1 wherein the pitch β of a thread on the plunger is from 1.5 mm to 12 mm.

6. The injection device of claim 1 wherein the drive shaft comprises a ratchet arm that engages one of the teeth during dose setting.

7. The injection device of claim 1 wherein the drive shaft comprises a ratchet arm that is configured to engage one of the teeth during dose setting.

8. A fixed dose injection device comprising the following in combination,
   a. a housing comprising a removable cartridge holder configured to contain a cartridge of medicament; and
   b. a dose setting and injecting assembly comprising,
      i. a rotatable gear having only two teeth offset from each other at an angle α that corresponds to only one predetermined fixed dose of medicament, where the rotatable gear is fixed axially in the housing;
      ii. a plunger threadedly engaged with the rotatable gear having a pitch β that is matched with angle α so that the plunger moves distally during dose delivery a distance corresponding to the predetermined fixed dose;
      iii. a torsional spring, and a drive shaft wherein the torsional spring rotates the drive shaft back to a zero position if the drive shaft is rotated by an angle smaller than α;
      iv. a trigger connected to the rotatable gear such that when the trigger is activated the torsional spring unwinds and causes the rotatable gear to rotate through angle α and to move the plunger distally to deliver the predetermined fixed dose;
      and
      vi. a reset dial configured to prevent rotation of the plunger and to allow the plunger to be retracted proximally into the housing when the cartridge holder is removed.

9. A fixed dose titration injection device comprising the following in combination,
   a. a housing comprising a removable cartridge holder configured to contain a cartridge of medicament; and
   b. a dose setting and injecting assembly comprising,
      i. a rotatable gear having only a first, a second, and a third tooth offset from each other at an angle α that corresponds to only one predetermined fixed dose of medicament such that only three injections of medicament can be performed using the cartridge of medicament, where the rotatable gear is fixed axially in the housing;
      ii. a drive shaft having a ratchet arm that is configured to engage either the first, the second or the third tooth during dose setting;
      iii. a plunger threadedly engaged with the rotatable gear having a pitch β that is matched with angle α so that the plunger moves distally during dose delivery a distance corresponding to one or more multiples of the predetermined fixed dose;
      iv. a torsional spring wherein the torsional spring rotates the drive shaft back until the ratchet arm engages at the next gear tooth, corresponding to the next lower dose, if a dose is dialed in between two fixed titration doses; and
      v. a trigger connected to the rotatable gear such that when the trigger is activated the torsional spring unwinds and causes the rotatable gear to rotate through one or more multiples of angle α and to move the plunger distally to deliver the one or more multiples of the predetermined fixed dose,
      and
      vii. a reset dial configured to prevent rotation of the plunger and to allow the plunger to be retracted proximally into the housing when the cartridge holder is removed.

\* \* \* \* \*